United States Patent [19]

Denbow

[11] 4,258,736
[45] Mar. 31, 1981

[54] ELECTROSTATIC MONITORING SYSTEM

[75] Inventor: Nicholas J. Denbow, Uxbridge, England

[73] Assignee: Bestobell Mobrey Limited, Slough, England

[21] Appl. No.: 71,263

[22] Filed: Aug. 30, 1979

[30] Foreign Application Priority Data

Sep. 6, 1978 [GB] United Kingdom ............... 35816/78

[51] Int. Cl.³ ............................................. H05F 1/00
[52] U.S. Cl. ........................................ 137/2; 361/215;
137/487.5; 137/551
[58] Field of Search ............... 361/215; 137/1, 2, 551,
137/487.5, 486; 116/67 R

[56] References Cited

U.S. PATENT DOCUMENTS

| 2,315,805 | 4/1943 | Mayo | 361/215 X |
| 3,160,785 | 12/1964 | Munday | 361/215 |
| 3,164,747 | 1/1965 | Yahnke | 361/215 |

Primary Examiner—Alan Cohan

[57] ABSTRACT

A system for monitoring a low conductivity liquid carrying an electrostatic charge and flowing along a pipeline comprises two separately insulated conductive wall sections ($M_1$, $M_3$) of the pipeline one downstream of the other. Means are connected to each of these sections for providing a signal representing the relaxation current released from the liquid to each of the wall sections and these signals are processed to provide indications or controls dependent upon the conductivity of the liquid, the relaxation time of the liquid, the streaming current, or the charge density carried by the liquid.

20 Claims, 3 Drawing Figures

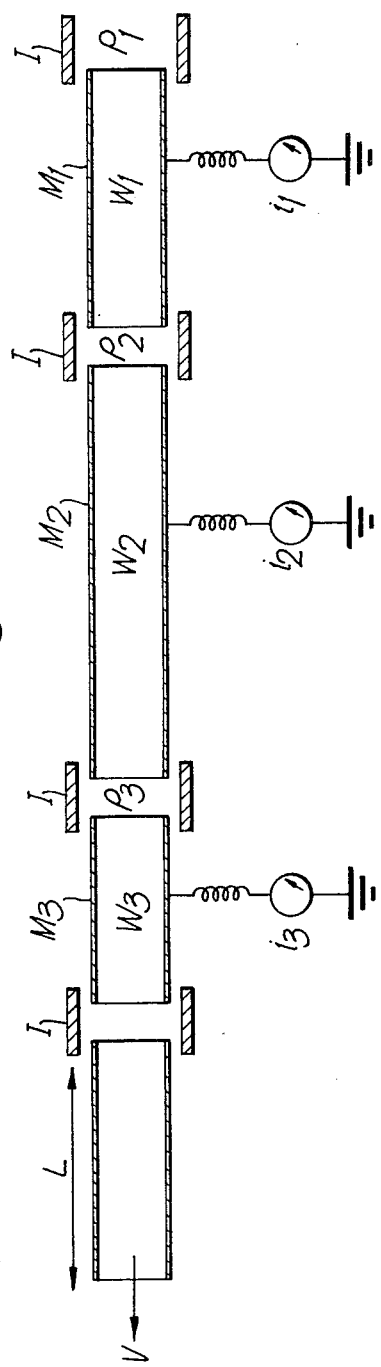
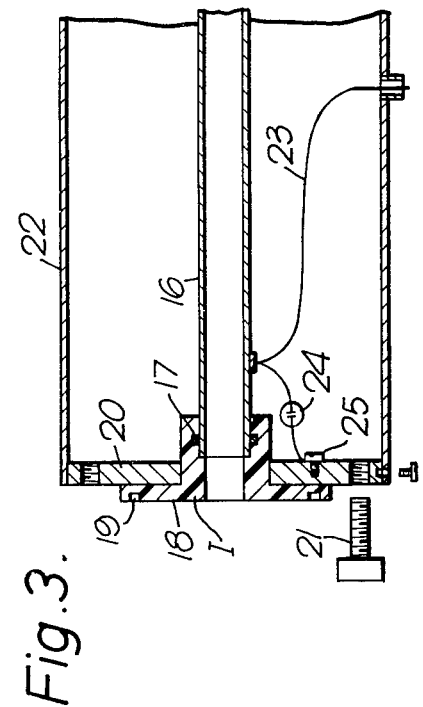

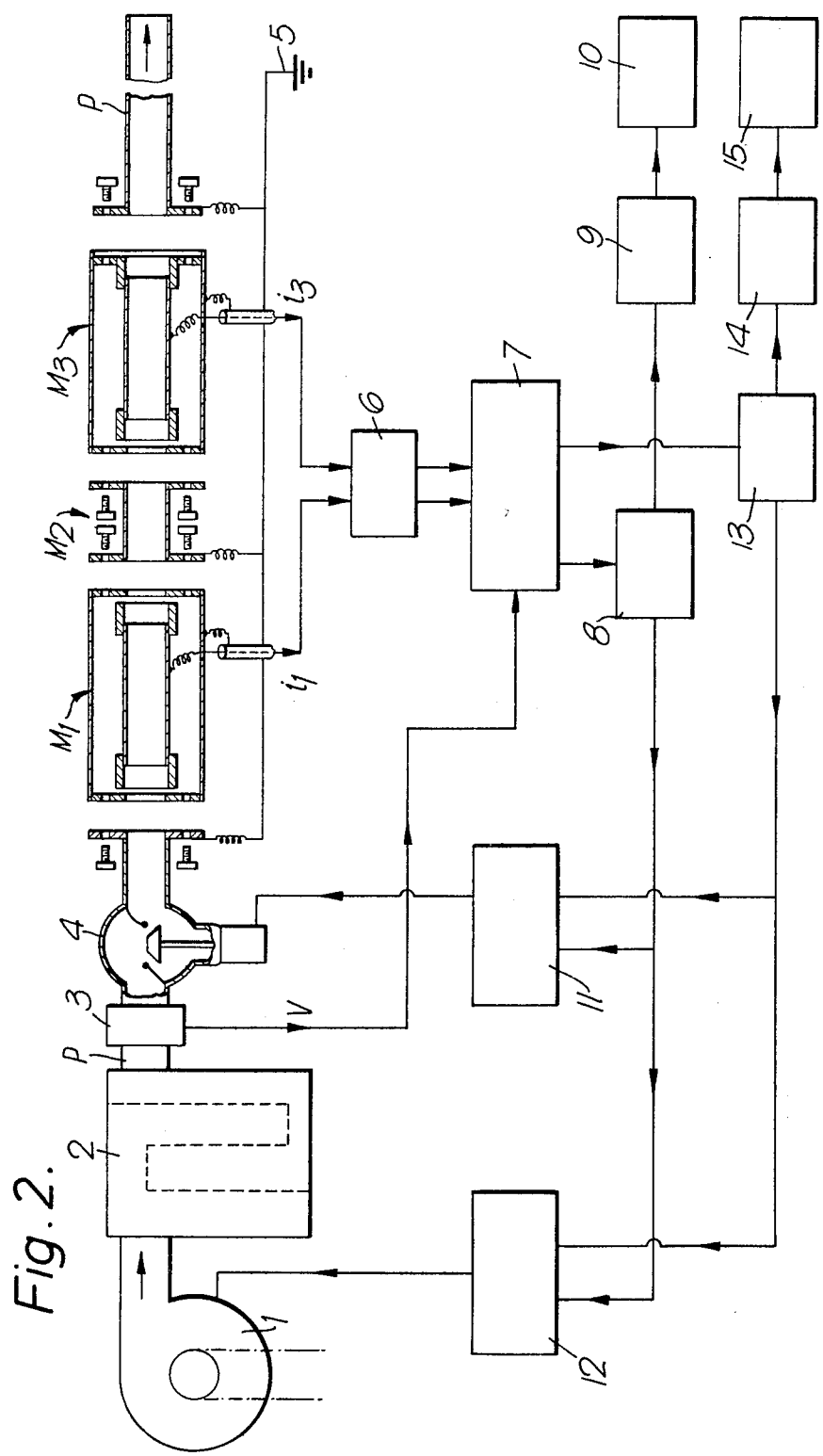

ELECTROSTATIC MONITORING SYSTEM

The invention relates to a system for monitoring an electrical charge-carrying, low conductivity liquid, such as a hydrocarbon fuel, flowing in a pipeline, whereby measurements and deductions related to the charge can be made.

In the flow of any relatively low conductivity liquid, electrostatic charge is present in the liquid from two sources. One is the electrostatic charge effectively generated by "friction" between the liquid and the pipe wall, normally predicted by the Schön equation, and normally fairly low in magnitude, for example 5 micro Coulombs per cubic meter per meter per second flow velocity. The second is charge generated in other devices in the pipeline, such as filters, valves or pumps. Filters can be prolific charge generators, and levels of 1000 micro Coulombs per cubic meter have been reported from this source.

The liquid continuously relaxes its hold on the charge which it carries, at a rate dependent upon the conductivity of the liquid and the charge density, the released charge being conducted away by the walls of the pipeline.

For any section of pipeline of volume $W(m^3)$, a liquid flowing with flow rate $V(m^3/sec)$ having a charge density $\rho$ ($\mu C/m^3$) on entry into the section of pipeline, gives a current relaxing to the walls of this section of magnitude $i$ ($\mu A$) where $$i = \rho V\{1 - \exp(-W/V\tau)\} \quad (1)$$

where $\tau$ is the relaxation time of the liquid, defined by $$\tau = \epsilon_r \epsilon_o / \delta \text{(secs)} \quad (2)$$

where $\epsilon_r$ is the dielectric constant or relative permittivity of the liquid, $\epsilon_o$ is the permittivity of free space, and $\tau$ is the conductivity of the liquid. In practice $\epsilon_r = 2$, $\epsilon_o = 8.854 \times 10^{-12}$ and $\delta$ varies from around 0.1 to $500 \times 10^{-12}$ S/m.

In the steady state of an effectively infinitely long pipeline, the "friction" current flowing into the liquid balances the "relaxation" current flowing out, giving no net current through a section of pipe wall. However, if the pipe is not infinite, and a charge generator such as a microfilter is situated upstream of the section of pipe considered, the charge level in the liquid ($\rho$) will exceed the steady state charge density ($\rho o$). Since a section of pipewall provides a current into the liquid which balances the relaxation from a charge density of $\rho o$ the net output current from a section of pipe wall will be given by $$i = (\rho - \rho o)V\{1 - \exp(-W/V\tau)\} \quad (3)$$

If, as has previously been proposed, the section of pipe in which the relaxation current is measured is a section with a diameter larger than the rest of the pipeline, the effective steady state charge density is reduced. For example for a diameter expansion ratio of 2, the steady state charge density is reduced to $\rho o \div 4$. In this case the current output of the insulated section of enlarged diameter is now:

$$i = (\rho - (\rho o/4))V\{1 - \exp(-W/V\tau)\} \quad (4)$$

and since $\rho o \div 4$ is considered negligible this term is sometimes ignored.

It has now been appreciated that if the relaxation current from two separate sections of the pipeline, downstream of one another, are monitored, the difference between these currents represents the relaxation which has occured in the upstream section plus any intervening section of the pipeline, and allows a derivation of the term $$\{1 - \exp(-W/V\tau)\} \quad (5)$$

which can be used as an indicator of the charge decay resulting from the relaxation currents, therefore giving an indication of the hazard inherent in the fuel arising from $\tau$, and can further be used in equation (1) or (3) to provide an output of $\rho V$ or $(\rho - \rho o)V$, giving the charge transported along the pipeline in the fuel or liquid in micro Coulombs per second. This can be thought of as a current flowing with the fuel and has sometimes been referred to as a "streaming" current.

In accordance with the present invention, a system for monitoring an electrostatic charge-carrying low conductivity liquid flowing along a pipeline comprises two separately insulated conductive wall sections of the pipeline, one downstream of the other, and means connected to each of the sections for providing a signal representing the relaxation current released, in use, from the liquid to each of the wall sections.

Means for measuring each relaxation current is most simply a line connected to earth and incorporating a current meter.

The wall sections of the pipeline may have a cross section greater than the rest of the pipeline but this is not necessary.

The two wall sections of the pipeline may be immediately adjacent to, but insulated from, one another. However, a comparison of the two relaxation currents will be more accurate, taking account of signal to noise if they are separated by an intervening conductive section from which a relaxation current released from the liquid, in use, to that wall section is drawn for example by connection of the section to earth.

The invention will now be described in more detail with respect to the accompanying drawings, in which:

FIG. 1 shows three sections of a pipeline diagrammatically;

FIG. 2 shows diagrammatically a typical pipeline installation with associated processing and control circuitry; and, FIG. 3 is a diagrammatic section through part of a monitor section of the FIG. 2 system.

FIG. 1 shows three sections $M_1$, $M_2$, and $M_3$ of pipeline, separated by insulators I, and carrying a flowing liquid, with relevant parameters of volume $W$, charge density $\rho$ and relaxation current $i$ indicated by the suffices 1, 2, and 3. Flow rate $V$ and relaxation time $\tau$ are constant. Sections $M_1$ and $M_3$ will later be considered as insulated current monitoring sections of pipeline and section $M_2$ will be considered as an intervening section of earthed conducting pipe.

Using equation (1) where $\rho$ is recognised as equivalent to $\rho - \rho o$ (or $\rho - \rho o/4$ if the section has a diameter twice that of the pipeline), $$i_1 = \rho_1 V\{1 - \exp(-W_1/V\tau)\} \quad (6)$$

$$i_2 = \rho_2 V\{1 - \exp(-W_2/V\tau)\} \quad (7)$$

$$i_3 = \rho_3 V\{1 - \exp(-W_3/V\tau)\} \tag{8}$$

and $$\rho_2 = \rho_1 \exp(-W_1/V\tau) \tag{9}$$

$$\rho_3 = \rho_2 \exp(-W_2/V\tau) \tag{10}$$

Equations (9) and (10) arise from the conservation of charge between the liquid charge density entering the section of pipeline and the charge density on leaving plus that which has relaxed to the walls. Therefore $$\frac{i_3}{i_1} = \exp\{-(W_2 + W_1)/V\tau\} \frac{1 - \exp(-W_3/V\tau)}{1 - \exp(-W_1/V\tau)} \tag{11}$$

For the particular case where $W_1 = W_3$, this reduces to $$i_3/i_1 = \exp\{-(W_2+W_1)/V\tau\} \tag{12}$$

This expression can be substituted in equation (6) to (8), for example with equation (6):

$$\rho_1 V = i_1/\{1 - (i_3/i_1)^x\} \tag{13}$$

where x is the ratio $W_1/W_1+W_2$, or with equation (8):

$$\rho_3 V = i_3/\{1 - (i_3/i_1)^x\} \tag{14}$$

where x is the ratio $W_3/W_1+W_2$. In both cases when $W_1 = W_3$, x is a constant.

The use of two monitoring sections taking measurements, $i_1$ and $i_3$ can be seen to provide useful information for electrostatic hazard monitoring and alarms with pumped liquids, particularly fuels.

The system may therefore usually comprise means responsive to the signals representative of the relaxation currents released to the upstream and downstream wall sections to derive a further signal dependent upon the charge decay in the liquid resulting from the release of the relaxation currents to the conductive wall sections and hence representative of the conductivity of the liquid.

Equation (12) gives a reading of the ratio between the charge densities at two separated positions in the pipeline. If this ratio is close to unity given the correct choice of $W_2+W_1$ in relation to V, then this ratio can indicate that the electrostatic charge at the first section is retained in the fuel at the second. This implies that the fuel conductivity is very low, making $\tau$ large. This is an indication of a possibly hazardous type of fuel, since any charge in the fuel at the measurement points will not decay away naturally before the fuel reaches a delivery vehicle, tanker, aircraft, etc., and could lead to electrostatic discharges in these areas.

Accordingly, the further signal dependent upon the charge decay and representative of the conductivity of the liquid may be representative of the ratio of the relaxation current released to the downstream wall section divided by the relaxation current released to the upstream wall section, or of the inverse of that ratio.

The further signal may be presented visually or may operate a hazard alarm when the ratio approaches unity, for example exceeds a predetermined threshold such as 0.75, and/or may operate an automatic control to control the flow velocity V, specifically to reduce the or to cut off the flow when a hazardous condition is recognized.

It will be appreciated that $\rho$ and hence $\rho_o$ is divided out in the reduction to equation (12) so that no inaccuracies resulting from the ignorance of $\rho_o$ arise. The exception is if the currents $i_1$ and $i_3$ are both very small and of the same order of magnitude as the absolute relaxation current. In that case the approach of the ratio to unity does not necessarily infer that a hazardous situation exists and it may then be necessary for the absolute relaxation current value to be taken account of in any readout or automatic control.

The system may also have calibration or other provision for the effective input of values of the fixed volumes $W_1$, $W_3$, and, when there is an intervening section, $W_2$ as well, and provision for input of the variable flow rate V. The system may then be arranged to provide a derivation of the relaxation time $\tau$ or the liquid conductivity $\delta$.

In practice this might be achieved if the system further includes a flowmeter and an indicator, the means for deriving the further signal also being responsive to an output of the flowmeter representing the velocity of liquid flow along the pipeline and the indicator being responsive to the further signal and being calibrated to give a quantitative value for the relaxation time of the liquid or its conductivity. The calibration would then take account of the fixed volume values.

Equations (13) and (14) can be used to give a reading of $\rho V$ or the amount of charge per unit time, i.e. the streaming current, flowing down the pipeline, at the measurement point chosen. This is an indication of the electrostatic hazard level of the fuel at this point.

If the volume of pipeline from the downstream pipe section to a discharge to a tank or vehicle is L, and $y = L/W_2 + W_1$, then a further parameter $$\rho_L V = \rho_3 V \left(\frac{i_3}{i_1}\right)^y = i_3 \left(\frac{i_3}{i_1}\right)^y / \left\{1 - \left(\frac{i_3}{i_1}\right)^x\right\} \tag{15}$$

can be used to give a measure of $\rho_L V$ or the actual streaming current carried with the fuel into the receiving tank. In practice the downstream monitoring section will probably be close to the discharge from the pipeline, i.e. $\rho_3$ will be equivalent to $\rho_L$ because L is very short. However, this will not always be so and the system may be provided with calibration to take account of the value L and have means for deriving the product $\rho_L V$. The system may therefore include means responsive to the signals representing the relaxation currents released to the upstream and downstream wall sections to derive a further signal representative of the streaming current carried by the liquid at a selected point in the pipeline.

The further signal representative of the streaming current may be presented visually or may operate a hazard warning if the product exceeds a predetermined threshold to up to, say, 1 $\mu A$, and may operate an automatic control to reduce or cut off the flow velocity V. Although in this case $\rho$ includes $\rho_o$, this involves no serious inaccuracy as with typical practical liquids, flow velocities and pipeline dimensions, $\rho_o$ is negligible and would have not effect on the setting of a hazard threshold for the streaming current.

The system may also include an input for the flow velocity V and be arranged to derive a value for $\rho$ alone.

The invention also includes a method of monitoring a low conductivity liquid flowing along a pipeline and carrying an electrostatic charge, the method comprising obtaining signals representative of the relaxation currents released from the liquid to respective wall sections of the pipeline, which sections are longitudinally offset along the pipeline; and processing the signals to provide a further signal representative of the conductivity of the liquid or of the streaming current.

Other potentially useful hazard parameters are $\rho/\delta$ or $\rho V/\delta$ and the system may be provided with means for deriving signals representative of these ratios in dependence upon the inputs already referred to. For certain quantitative derivations, it may be necessary to know the internal volumes of the pipe sections but these will normally be constant and measureable. It will also be necessary, as already mentioned, to know the liquid flow velocity and this can be measured by means of a conventional flowmeter in the pipeline.

FIGS. 2 and 3 show diagrammatically a system in accordance with the invention and including many of the optional controls and derivations referred to. Where appropriate similar parts are given the same reference characters as in FIG. 1.

As shown in FIG. 2 the system incorporates a pipeline P with insulated conductive sections formed by parts of an upstream monitor $M_1$, a downstream monitor $M_3$, and an intermediate section $M_2$. These sections are shown exploded in FIG. 2.

Fuel or other liquid is fed along the pipeline from a pump 1, through a filter 2, which may be a prolific charge generator. The pipeline then incorporates in series between the filter 2 and monitor $M_1$, a flowmeter 3, and flow control valve 4. The downstream end of the pipeline may lead, for example, to a tanker.

The pipeline and monitor casings are earthed through a connection 5. The relaxation currents received by the monitor sections $M_1$ and $M_3$ respectively are fed to a conventional circuit 6 for providing output signals representing the two relaxation currents. These signals are fed into an electronics processing circuit 7, which may also be fed with a signal representing the flow velocity V, from the flowmeter 3. The unit 7 will be a conventional mathematical processing circuit, such as an integrated circuit, or microprocessor device to solve the relevant equations previously referred to. A relaxation current ratio output may thus be fed to a unit 8 from which the value of the ratio is displayed or gives an analogue output at a unit 9, or operates an alarm 10 when a predetermined threshold is exceeded. Similarly the signal from the unit 8 may be fed back via a control unit 11 which controls the valve 4 to adjust or cut off the liquid flow in dependence upon the extent of any potential hazard sensed. Similarly a signal from the unit 8 may be fed to a control unit 12 to adjust the flow velocity by adjusting the speed of the pump 1, rather than controlling the valve 4.

In analogous fashion a signal representing the streaming current may be supplied from the processing circuit 7 to a unit 13, this unit feeding a corresponding signal to a display or analogue output unit 14 or alarm 15, similar to the units 9 and 10, and/or supply a control signal to the control units 11 and/or 12 to control the valve and/or pump.

As shown in FIG. 3, each monitor section $M_1$ and $M_3$ comprising an inner conductive pipeline section 16, which carries the liquid directly and receives the relaxation current. Each section 16 is carried at its ends by polypropylene insulators I to which it is sealed by an O-sealing ring 17. The insulators I have radial flanges 18 carrying further O-sealing rings 19, the insulator flanges being compressed between mounting flanges 20 secured to complementary flanges of adjacent pipeline section by bolts 21. The mounting flanges 20 carry outer tubular casing sections 22 which act as electrostatic screens and physical supports for the internal parts.

The relaxation current is carried away from the conductive section 16 via a coaxial cable 23 the outer sheath of which is earthed and the core of which is electrically connected to the section 16 by for example a jubilee clip or screw. A neon safety lamp 24 may also be provided in a circuit between the section 16 and an earth connection 25, the lamp being arranged to conduct at a threshold voltage of say 90 volts.

The radial clearance between the section 16 and casing 22 is exaggerated in FIG. 3 and in practice it would probably be much smaller although the outer casing may be common for a range of sizes of pipeline section 16 for use in different pipelines.

The following parameters indicate typical orders of magnitude.

(1) $V = 50$–400 GPM i.e. 3.8 to 30 liters per second.

(2) $\delta = 2$–400 pS/m i.e. $\tau = 8$ to 0.04 seconds.

For example, for commercial jet fuel $\delta = 50$–300 pS/m i.e. $\tau = 0.33$ to 0.06 seconds.

For diesel or USAF JP-4 fuel, without an antistatic additive, $\delta = 2$–50 pS/m i.e. $\tau = 8$ to 0.33 seconds.

(3) Pipleine diameters are normally '  inch i.e. 4.56 liters volume per meter length (so that at 400 GPM linear flow rate will be 6.6 m/sec. or 20 ft./sec.)

(4) If $V = 200$ GPM ($15 \times 10^{-3}$ m$^3$ per sec.), W = 0.5 m. of 3 inch pipe (2.3 liters or $2.3 \times 10^{-3}$ m$^3$, $\delta = 50$ pS/m ($\tau = 0.33$ sec.), $\rho = 100$ micro C/m$^3$, then equation (6) gives i = 600 nA. If then $\delta$ were changed to 10, then i would become 120 nA. If W were then 0.3 m. of 3 inch pipe (1.4 liters), and $\delta = 50$ pS/m, then i would become 360 nA. If $\delta$ were then changed to 10 pS/m, i would become 72 nA.

(5) If the relaxation currents $i_3$ and $i_1$ are noisy, a suitable ratio is considered to be less than 0.75. To achieve an exponential of $e^{-x} < 0.74$, then x must be $> 0.3$. Values of $W_1$ and $W_2$ would then be chosen such that equation (12) has an exponent greater than 0.3.

A. COMMERCIAL JET FUEL.

If $i_3/i_1 = \exp\{-(W_2+W_1)/V\tau\}$, is to be $< 0.74$ then $(W_1+W_2)/V\tau$ must be $> 0.3$. For:

| $\tau$ (secs) | V (LPS) | $W_1 + W_2$ (Liters) | $(W_1 + W_2)/V\tau$ |
| --- | --- | --- | --- |
| .33 | 30 | 10 | 1 |
|  |  | 5 | 0.5 |
|  |  | 3 | 0.3 |
| .2 | 30 | 5 | 0.83 |
|  |  | 3 | 0.5 |
| .33 | 10 | 10 | 3 |
|  |  | 5 | 1.5 |
|  |  | 3 | 1.0 |

Therefore for commercial jet fuel a pipe length of 5 liters capacity (1.1 meter Length) would give adequate residence times between sensors to produce useful results. Each sensor could be around 30 cm. long, with the inter sensor space around 90 cm. (i.e. 30 cm.+90 cm.=1.2 m. which is >1.1 m.)

Alternatively the table shows that 3 liters of capacity (0.7 meter of pipe length) should just be sufficient to give a ratio $i_3/i_1$ of less than 0.74. A system could now be used with $W_2 = 0$, i.e. no intervening earthed pipe section between the two sections with sensors measuring $i_1$ and $i_3$, and $W_1 = W_3 = 3$ liters or 70 cms. in length. The two measurement sections are now adjacent and the calculation of $\rho V$ is therefore simplified.

B. U.S.A.F. JP-4 FUEL.

| $\tau$ (secs) | V (LPS) | $W_1 + W_2$ (Liters) | $(W_1 + W_2)/V\tau$ |
|---|---|---|---|
| 8 | 30 | 240 | 1 |
|   |    | 120 | .5 |
|   |    | 80  | .33 |
| 4 | 30 | 120 | 1 |
|   |    | 40  | .33 |
| 4 | 10 | 120 | 3 |
|   |    | 40  | 1 |
| 1 | 30 | 120 | 4 |
|   |    | 40  | 1.33 |

Therefore for JP-4 to measure down to 2 pS/m ($\tau = 8$ secs) the separation between sensors must represent at least 80 liters fuel. For a 3" line this is 17 meters long (50 feet). This represents approximately one length of hose.

Electronic filtering of the signals can enable signal ratios approaching unity to be measured reliably so that the volume and separation of the sections to which the sensors are connected may be reduced.

I claim:

1. A system for monitoring an electrostatic charge-carrying low conductivity liquid flowing along a pipeline, said system comprising two separately insulated conductive wall sections of said pipeline, one downstream of the other and means connected to each of said sections for providing a signal representing the relaxation current released, in use, from the liquid to each of said wall sections.

2. A system according to claim 1, in which said means for measuring each relaxation current is a line connected to earth and incorporating a current meter.

3. A system according to claim 1, in which said two wall sections of said pipeline are separated by an intervening conductive wall section from which a relaxation current released from the liquid, in use, to said intervening wall section is drawn.

4. A system according to claim 1, which comprises means responsive to said signals representative of said relaxation currents released to said wall sections to derive a further signal dependent upon the charge decay in said liquid resulting from the release of said relaxation currents to said conductive wall sections, and hence representative of the conductivity of said liquid.

5. A system according to claim 4, in which said further signal is representative of the ratio of said relaxation current released to said downstream one of said wall sections divided by said relaxation current released to the other of said wall sections, or of the inverse of said ratio.

6. A system according to claim 5, in which said further signal is adapted to operate an alarm when said ratio exceeds a predetermined value.

7. A system according to claim 4, including means responsive to said further signal for controlling the flow of liquid along said piepline.

8. A system according to claim 4, further including a flowmeter and an indicator, said means for deriving said further signal also being responsive to an output of said flowmeter representing the velocity of liquid flow along said pipeline and said indicator being responsive to said further signal and being calibrated to give a quantitative value for the relaxation time of said liquid or its conductivity.

9. A system according to claim 1, including means responsive to said signals representing said relaxation currents released to said wall sections to derive a further signal representative of the streaming current carried by said liquid at a selected point in said pipeline.

10. A system according to claim 9, in which said further signal is adapted to operate an alarm when said streaming current exceeds a predetermined value.

11. A system according to claim 9, including means responsive to said further signal for controlling the flow of liquid along said pipeline.

12. A system according to claim 9, further comprising an indicator which is responsive to said further signal and is calibrated to give a quantitative value for said streaming current.

13. A system according to claim 9, further including a flowmeter providing, in use, an output signal representing the velocity of liquid flow along said pipeline, and means for processing said further signal together with said flowmeter output signal to derive a third signal representative of the charge density carried by said liquid at a selected point in said pipeline.

14. A system according to claim 13, in which said third signal is adapted to operate an alarm when said charge density exceeds a predetermined value.

15. A system according to claim 13, including means responsive to said third signal for controlling the flow of liquid along said pipeline.

16. A system according to claim 13, further including an indicator which is responsive to said third signal and is calibrated to give a quantitative value for said charge density.

17. A system according to claim 9, in which said selected point in the pipeline is an outlet of said pipeline downstream of said downstream wall section.

18. A method of monitoring a low conductivity liquid flowing along a pipeline and carrying an electrostatic charge, said method comprising obtaining signals representative of the relaxation current released from said liquid to respective wall sections of said pipeline, which sections are longitudinally offset along the pipeline; and processing said signals to provide a further signal representative of the conductivity of said liquid or of the streaming current.

19. A method according to claim 18, in which said further signal is used to control the rate of flow of the liquid along said pipeline.

20. A method according to claim 19, in which the flow velocity of said liquid along said pipeline is sensed and a corresponding velocity signal obtained and said further signal is processed together with said velocity signal to obtain a value for the relaxation time of said liquid or its conductivity or the charge density carried by said liquid.

* * * * *